(12) United States Patent
Hiejima et al.

(10) Patent No.: US 7,470,262 B2
(45) Date of Patent: Dec. 30, 2008

(54) MEDICAL VALVE

(75) Inventors: Katsuhiro Hiejima, Osaka (JP); Ken Suzuki, Osaka (JP); Kazuyoshi Harada, Osaka (JP); Takuya Masuda, Osaka (JP)

(73) Assignee: Nipro Corporation, Osaka (JP)

( * ) Notice: Subject to any disclaimer, the term of this patent is extended or adjusted under 35 U.S.C. 154(b) by 428 days.

(21) Appl. No.: 10/800,913

(22) Filed: Mar. 16, 2004

(65) Prior Publication Data
US 2004/0186458 A1    Sep. 23, 2004

(30) Foreign Application Priority Data
Mar. 17, 2003    (JP)    ............................. 2003-071260

(51) Int. Cl.
*A61M 35/00*    (2006.01)
(52) U.S. Cl. .................. 604/289; 604/249; 604/167.04; 604/256
(58) Field of Classification Search ............ 604/167.03, 604/167.04, 167.01, 170.01, 411, 412, 256, 604/249, 289
See application file for complete search history.

(56) References Cited
U.S. PATENT DOCUMENTS
5,514,116 A    5/1996    Vaillancourt et al.    ........ 604/283

| | | | |
|---|---|---|---|
| 5,549,566 A * | 8/1996 | Elias et al. ............. | 604/167.03 |
| 6,029,946 A | 2/2000 | Doyle ....................... | 251/149.1 |
| 6,050,978 A | 4/2000 | Orr et al. .................... | 604/249 |
| 2003/0032940 A1 | 2/2003 | Doyle .......................... | 604/533 |

FOREIGN PATENT DOCUMENTS
EP    0 681 493 B1    11/1995
JP    7-505064 A    6/1995

* cited by examiner

*Primary Examiner*—Jacqueline F. Stephens
(74) *Attorney, Agent, or Firm*—Kubovcik & Kobovcik (57) ABSTRACT

A medical valve includes: (a) a housing having a hollow body opened at the top end, wherein the tip of a male luer is to be removably inserted in the housing; (b) a spike disposed to extend longitudinally in the housing, the spike except at least the top end portion being formed in an approximately tapered shape in which its outside diameter becomes progressively smaller toward the top end portion, wherein a fluid transferring passage, which is opened radially outwardly, is formed to extend longitudinally in the spike; and (c) an elastic seal having an elastically deformable tubular shape fitted on the spike to seal the spike, the elastic seal including a top end portion having an openable/closable portion to be openably closed over the spike, wherein the elastic seal is elastically deformed to be downwardly shrunk by downward pressure due to the tip of the male luer.

9 Claims, 12 Drawing Sheets

MEDICAL VALVE

FIELD OF THE INVENTION

The present invention relates to a medical valve which makes it possible to perform supply of a fluid and the like through the connection of a male luer without using a metal needle because of the problem of erroneous needle sticking and the like by an operator, in a mixing plug which is provided in a fluid circuit, for example, a fluid infusion bag, an intermediate portion of a fluid infusion line (route) or an external fluid circuit, for the purposes of effecting supply, mixing, additional administration of medicament solutions such as trace elements, vitamins and antibiotics.

DESCRIPTION OF THE RELATED ART

As a medical valve in which a male luer such as a syringe or other fluid circuit is connected to a fluid infusion route without using a metal needle, there is a medical valve in which a spike contained in a housing is covered with an elastic seal (refer to, for example, JP-T-7-505064, EP 0681493B1, U.S. Pat. No. 6,029,946).

In this construction, by the application of pressure by a tip of a male luer, the elastic seal is compressed downwardly and the spike is inserted through the elastic seal and is exposed upwardly to enter the tip of the male luer. In this manner, the inside of the male luer and a fluid transferring passage inside the spike communicate with each other via an opening of a side surface of the spike, whereby a fluid can be transferred. In addition, when the application of pressure to the elastic seal by the tip of the male luer is cancelled, the elastic seal is expanded from its compressed state by its resilient force and is restored to the original size, whereby the spike is sealed in the elastic seal.

The spike is generally made of a resin in terms of cost. However, in the above-mentioned related art, the fluid transferring passage is formed in the inside of the spike and is completely covered with the peripheral wall portion of the spike, so that if the outside diameter of the spike is made small, there is a need for making the peripheral wall portion of the spike extremely thin, and in this case, it is extremely difficult to form the spike from a resin.

For this reason, it is more preferable that the inside diameter of the tip of the male luer which the spike enters becomes larger (for example, the inside diameter is 1.5 mm or more). However, if the male luer is a syringe made of glass and the tip is made of glass, it is difficult to enlarge the inside diameter of the tip in terms of the problem of molding, and in this case, there is the problem that the spike cannot be made to enter the tip and that the male luer and the medical valve cannot be connected to each other.

BRIEF SUMMARY OF THE INVENTION

As a result of earnest investigations made by the inventors to solve the problems associated with the conventional techniques, the invention has been completed.

An object of the invention is to provide a medical valve to which a male luer can be easily connected even if the inside diameter of the tip of the male luer is small.

The above-mentioned object and other objects of the present invention will be clarified further more in the following description, and these objects are attained by the present invention comprising the constitution mentioned below.

The invention relates to a medical valve to which a male luer is to be separably connected comprising:

(a) a housing having a hollow body opened at the top end, wherein the tip of the male luer is to be removably inserted in the housing;

(b) a spike disposed to extend longitudinally in the housing, the spike except at least the top end portion being formed in an approximately tapered shape in which its outside diameter becomes progressively smaller toward the top end portion, wherein a fluid transferring passage, which is opened radially outwardly, is formed to extend longitudinally in the spike, the bottom portion of the fluid transferring passage being connected to a fluid circuit; and (c) an elastic seal having an elastically deformable tubular shape fitted on the spike to seal the spike, the elastic seal comprising a top end portion having an openable/closable portion to be openably closed over the spike, wherein the elastic seal is elastically deformed to be downwardly shrunk by downward pressure due to the tip of the male luer, thereby the openable/closable portion is brought into abutment with the spike, and is elastically deformed to be opened radially outwardly to be fitted onto the spike, so that the inside of the male luer communicates with the fluid transferring passage of the spike.

The medical valve to which a male luer is to be separably connected may comprise:

(a) a housing having a hollow body opened at the top end, wherein the tip of the male luer is to be removably inserted in the housing;

(b) a solid spike disposed to extend longitudinally in the housing, the spike except at least the top end portion being formed in an shape approximately tapered upwardly, wherein a groove-shaped fluid transferring passage, which is opened radially outwardly, is formed to extend longitudinally in the peripheral surface of the spike, the bottom portion of the fluid transferring passage being connected to a fluid circuit; and (c) an elastic seal having an elastically deformable tubular shape fitted on the spike to seal the spike, the elastic seal comprising a top end portion having an openable/closable portion to be openably closed over the spike, wherein the elastic seal is elastically deformed to be downwardly shrunk by downward pressure due to the tip of the male luer, thereby the openable/closable portion is brought into abutment with the spike, and is elastically deformed to be opened radially outwardly to be fitted onto the spike, so that the inside of the male luer communicates with the fluid transferring passage of the spike.

The spike described below may be used instead of the spike described above.

For example, the spike may comprise:

(i) a joining portion constituting the top end portion of the spike; and (ii) a plurality of branch portions, which constitutes the remaining portion of the spike, formed integrally with the joining portion to branch off downwardly from the joining portion, and wherein the fluid transferring passage is defined between the branch portions.

The spike may comprise a plurality of divided bodies extending along the entire longitudinal length thereof, and wherein the fluid transferring passage is defined between the divided portions.

The spike may comprise:

(i) a plurality of main portions extending along the entire longitudinal length of the spike; and (ii) a bridge portion formed integrally with the main portions and disposed between the main portions to join the main portions together, wherein the fluid transferring passage is defined between the main portions.

The medical valve, to which a male luer is to be separably connected, may comprise:

(a) a housing having a hollow body opened at the top end, wherein the tip of the male luer is to be removably inserted in the housing;

(b) a spike disposed to extend longitudinally in the housing, the top end portion of the spike having an approximately cylindrical shape, the top end surface of the spike being an approximately hemispherical surface which is upwardly convex, the spike except the top end portion being formed in an approximately tapered shape in which the outside diameter becomes progressively smaller toward the top end, wherein a fluid transferring passage, which is opened radially outwardly, is formed to extend longitudinally in the peripheral surface of the spike, the bottom portion of the fluid transferring passage being connected to a fluid circuit;

(c) an elastic seal having an elastically deformable tubular shape fitted on the spike to seal the spike, the elastic seal comprising a top end portion having an openable/closable portion to be openably closed over the spike, wherein the elastic seal is elastically deformed to be downwardly shrunk by downward pressure due to the tip of the male luer, thereby the openable/closable portion is brought into abutment with the spike, and is elastically deformed to be opened radially outwardly to be fitted onto the spike, so that the inside of the male luer communicates with the fluid transferring passage of the spike.

The spike may comprise at least three fins projecting radially outwardly from the axial portion, and wherein the fluid transferring passages are defined between adjacent ones of the fins.

The fins may be circumferentially spaced from one another at equal intervals, the edge of each of the fins being placed in abutment with the inside surface of the elastic seal.

A portion of the elastic seal, which is brought in abutment with the fins, may have a cross section of an approximately polygonal shape.

The bottom portion of the spike may be inserted in and fixed to the housing.

The central portion of the bottom surface of the openable/closable portion may be made approximately flat and be opposed to the top end of the spike across a gap.

A ring-shaped projection, which projects radially inwardly and is placed in abutment with the top end portion of the spike, may be formed to extend around approximately the entire circumference of the inside surface of the top portion of the elastic seal.

The elastic seal except the openable/closable portion and the bottom end portion may have a bellows-shaped shrinkable portion.

The top end surface of the housing and the top end surface of the elastic seal may be made substantially flush with each other.

BRIEF DESCRIPTION OF THE DRAWINGS

FIGS. 1 to 5 show a first embodiment of the invention.

FIGS. 9 to 11 show a fifth embodiment of the invention.

FIGS. 12 to 17 show a sixth embodiment of the invention.

DETAILED DESCRIPTION OF THE INVENTION

Figure 1:
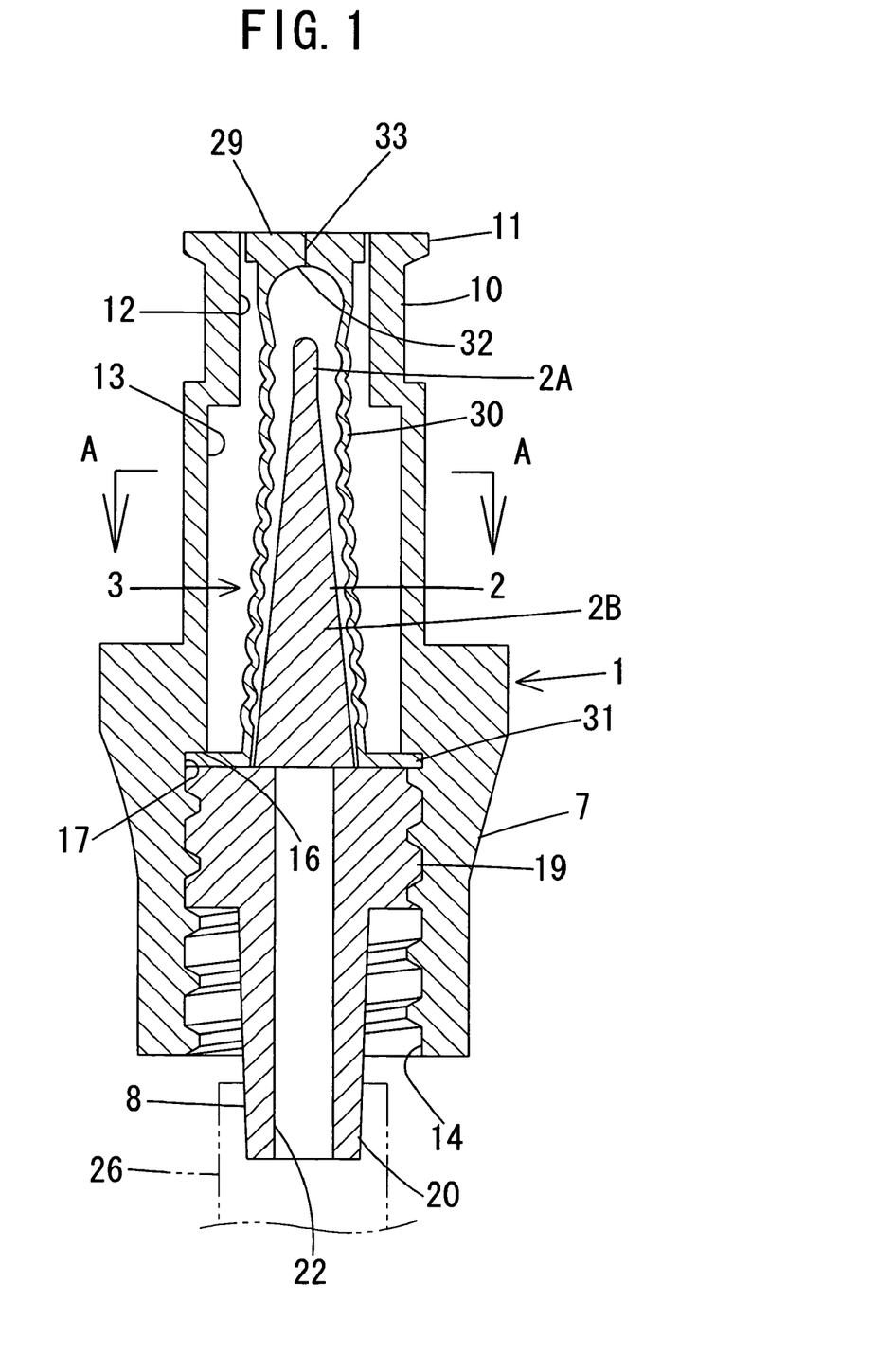
FIG. 1 is a cross-sectional view.
Figure 3:
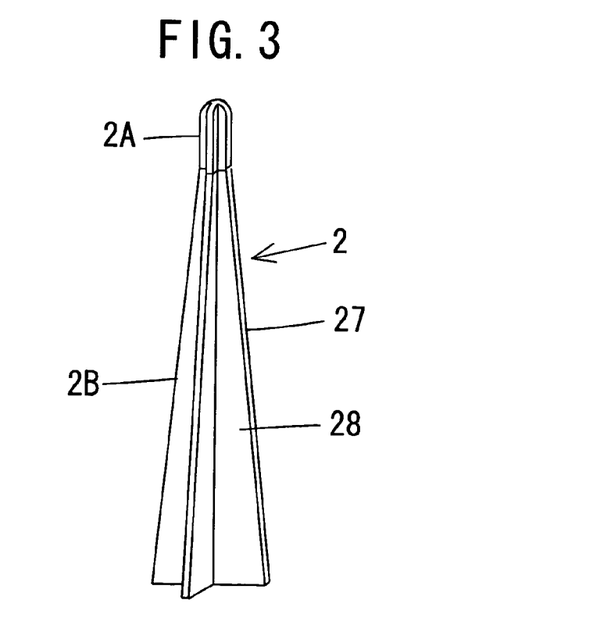
FIG. 3 is a perspective view of the spike of FIG. 1.
Figure 4:
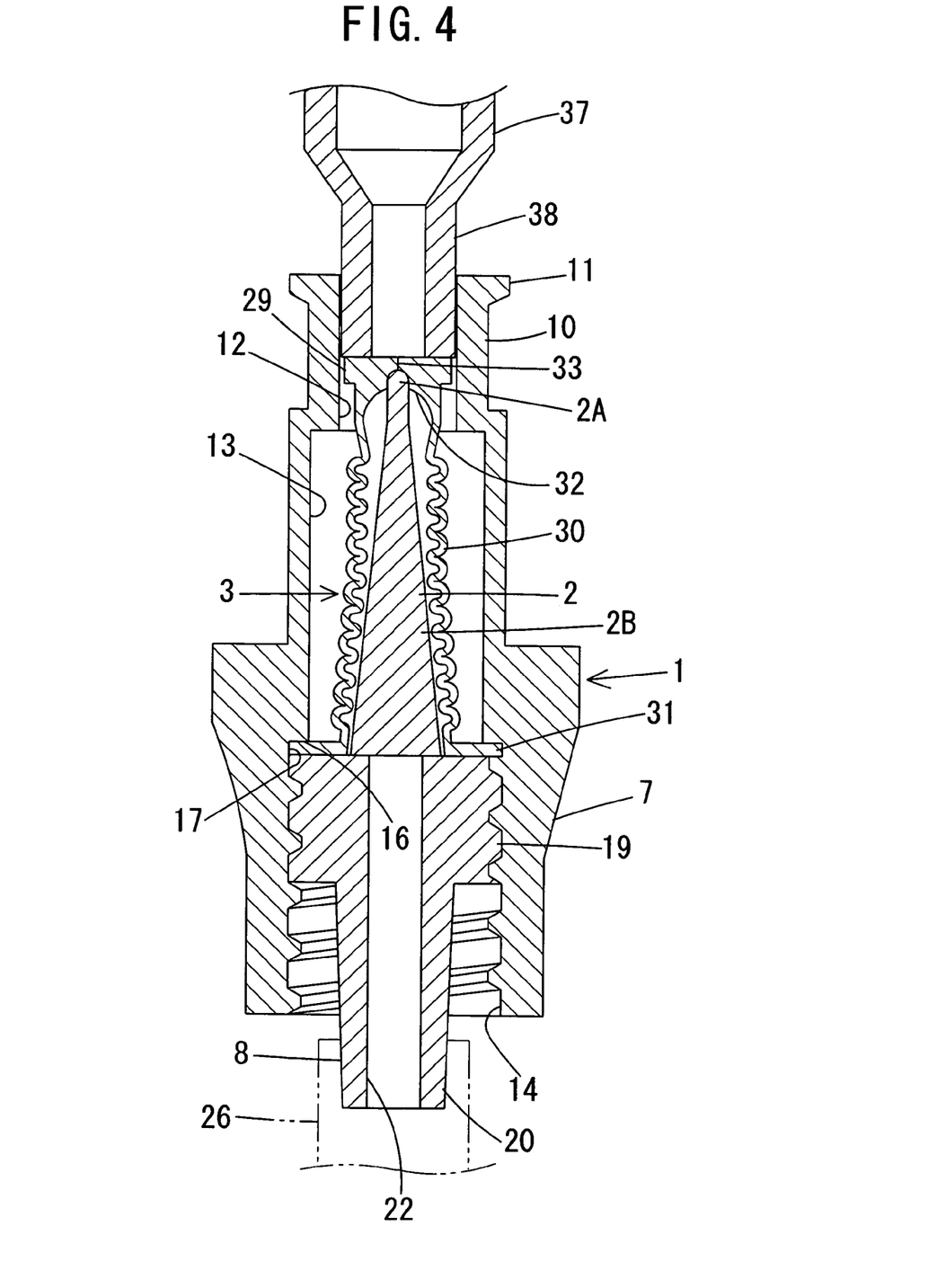
FIG. 4 is a view of the operating state of FIG. 1.
Figure 5:
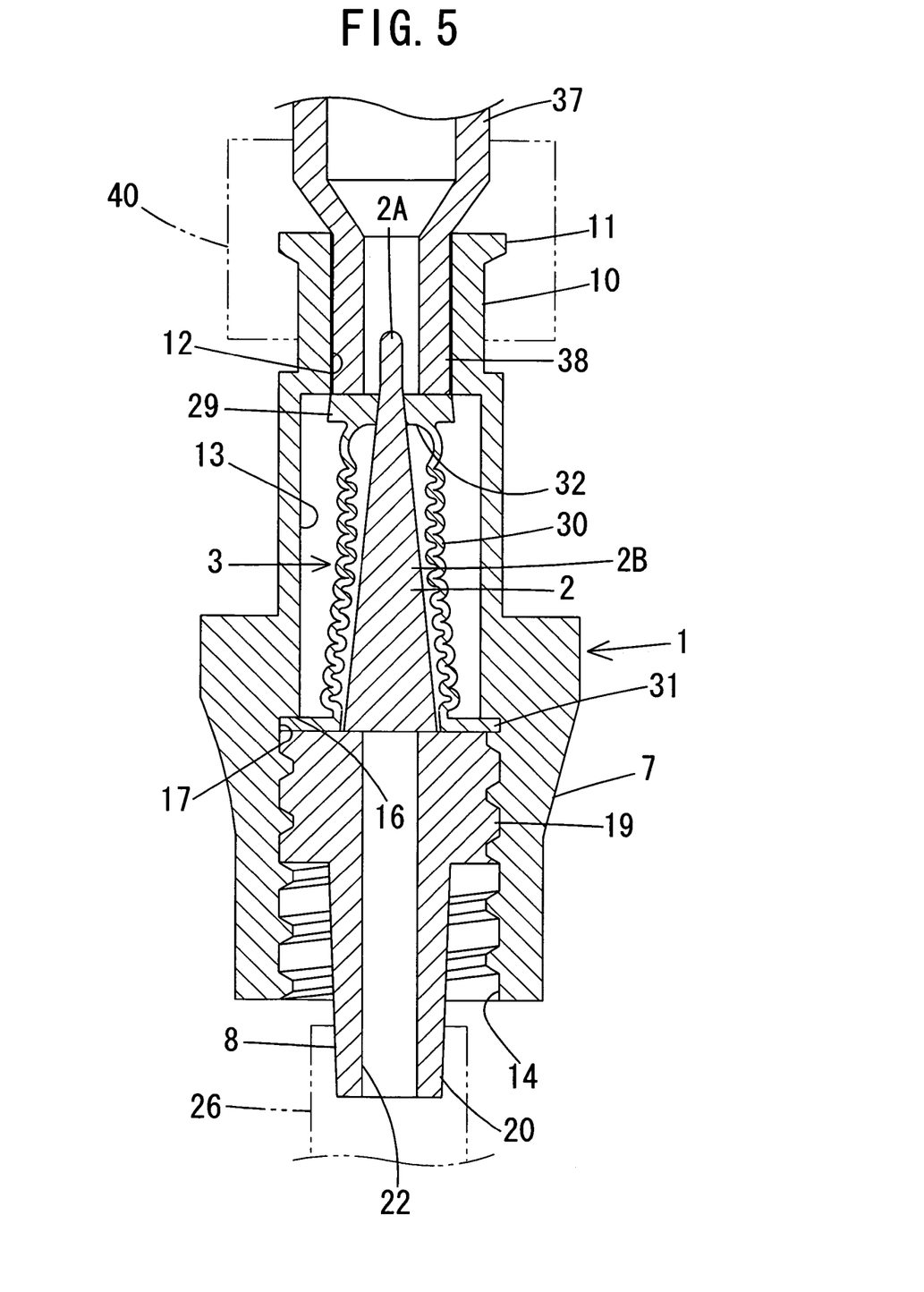
FIG. 5 is a view of the operating state of FIG. 4.

A first embodiment in which the invention is applied to a mixing plug will be described below with reference to FIGS. 1 to 5. FIGS. 1, 4 and 5 show a mixing plug, and the mixing plug has a housing 1, a spike (slit rod) 2, and an elastic seal (member) 3.

Figure 2:
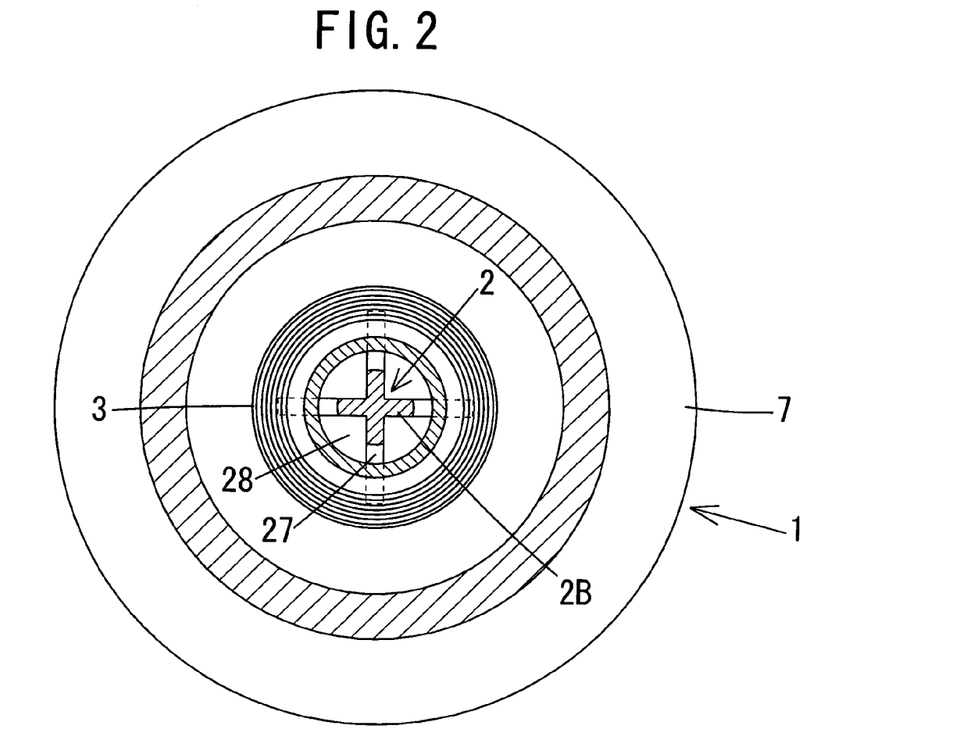
FIG. 2 is a cross-sectional view taken along line A-A of FIG. 1.

As also shown in FIG. 2, the housing 1 has a hollow shape opened at both top and bottom ends so that a male luer is removably inserted into the housing 1, and has a body 7 and a connector 8. Polycarbonate resins, acrylic resins, hard vinyl chloride resins, high-density polyethylene resins, polypropylene resins, acrylonitrile-butadiene-styrene block copolymer resins, polyamide resins, polyethylene telephthalate resins, polybuthylene telephthalate resins, polyacetal resins, fluororesins, polyphenylene sulfide resins, polyethersulfone resins, polyether ether ketone resins, liquid crystal polymeric resins and the like can be enumerated as the constituent materials of the body 7 and the connector 8. It is also possible to use reinforced materials prepared by compounding the above-noted resins with glass fibers, graphites, inorganic fillers, carbon nanotubes or the like. Furthermore, to improve the sterility of an upstream-side connecting portion 10 which will be described later, an antimicrobial agent (such as silver- or zinc-substituted zeorite or silver-supported calcium phosphate) may also be kneaded with the constituent material of the body 7 and the like.

The body 7 is made hollow at both top and bottom ends, and a top portion of the body 7 is made an upstream-side (male) connecting portion ((male) coupling means or (male) coupling portion) 10 to which a male luer is to be separably connected, and a male screw portion 11 is formed on the peripheral surface of the top portion. On the inside of the body 7, a small-diameter hole 12 which is made the inside surface of the upstream-side connecting portion 10, a large-diameter hole 13 which is made larger in diameter than the small-diameter hole 12, an engagement hole 17 which is made larger in diameter than the large-diameter hole 13, and a female screw portion 14 which is made equal in diameter to the engagement hole 17 and in which a female screw is formed are integrally formed to be arranged in named order in the downward direction. An abutment surface 16 which is formed in a stepped shape and has a surface formed to face down is formed at the boundary portion between the large-diameter hole 13 and the engagement hole 17.

The connector 8 has a hollow shape opened at both top and bottom ends, and is inserted and fixed in the bottom portion of the body 7. The connector 8 has a mating portion 19 and a downstream-side (male) connecting portion ((male) coupling means or (male) coupling portion) 20 which are integrally formed to be arranged in named order in the downward direction. The mating portion 19 has a male screw formed around its peripheral surface, and the downstream-side connecting portion 20 is made smaller in diameter than the mating portion 19. A communication hole 22 is formed to extend through the inside central portion of the connector 8 in the longitudinal direction.

The mating portion 19 is inserted and screwed into the female screw portion 14 of the body 7 and is fixed thereto. The downstream-side connecting portion 20 projects downwardly from the bottom end of the female screw portion 14 of the body 7 and is tapered in the downward direction, and a fluid transferring tube 26 shown by way of an example of a fluid circuit is separably connected to the downstream-side connecting portion 20. Incidentally, the fluid circuit includes not only the tubes of fluid infusion lines and external fluid circuits but also various solution bags such as blood transfusion bags, and various devices. Incidentally, the connector 8 may be bonded to the body 7 instead of being provided with the mating portion 19.

The spike 2 is disposed to extend in the inside of the body 7 in the longitudinal direction from the bottom portion of the small-diameter hole 12 through the large-diameter hole 13 to the top end portion of the female screw portion 14, and is uprightly set on and adhesively fixed to the mating portion 19 of the connector 8. As also shown in FIG. 3, the top end portion of the spike 2 is made a straight portion 2A having an approximately constant outside diameter, and the remaining portion is made a tapered portion 2B which is formed in an (approximately) tapered shape so that its outside diameter becomes progressively smaller toward the top end portion. Incidentally, the whole of the spike 2 may also be formed in an (approximately) tapered shape so that its outside diameter becomes progressively smaller toward its top end. The maximum outside diameter of the straight portion 2A is preferably approximately 0.5-2.0 mm because, for example, the inside diameter of a tip of a glass syringe used as a male luer is 1.0-2.5 mm. As the constituent material of the spike 2, not only the same resins as the body 7 but also metal materials such as stainless steel can be enumerated.

The spike 2 has at least three (in this embodiment, four) fins 27 which project radially outwardly from its axial portion. The fins 27 are circumferentially spaced from one another at equal intervals and extend through the entire longitudinal length of the spike 2, and longitudinal fluid transferring passages 28 are defined between adjacent ones of the fins 27. Each of the fluid transferring passages 28 is formed to extend through the entire longitudinal length of the spike 2, and is opened radially outwardly and is also opened at both top and bottom ends. The bottom end opening of each of the fluid transferring passages 28 communicates with the communication hole 22 of the connector 8. Incidentally, the fins 27 may also be disposed to extend over the entire longitudinal length of the spike 2 except the straight portion 2A.

The elastic seal 3 has an elastically deformable tubular (approximately cylindrical) shape, and is fitted onto the spike 2 from above to seal the spike 2. The elastic seal 3 includes an openable/closable portion 29, a shrinkable portion 30 and a flange portion 31 which are integrally formed to be arranged in named order in the downward direction. By downward pressure due to the tip of the male luer, the elastic seal 3 is elastically deformed to be downwardly shrunk, thereby the openable/closable portion 29 is brought into abutment with the spike 2, and is elastically deformed and opened radially outwardly to be fitted onto the spike 2, so that the tip of the male luer is allowed to communicate with the fluid transferring passages 28 of the spike 2. Natural rubber, synthetic polyisoprene rubber, butyl rubber, chloroprene rubber, silicone rubber, urethane rubber, styrene-butadiene rubber, ethylene propylene rubber, acrylic rubber, fluororubber, thermoplastic elastomers and the like can be enumerated as the constituent material of the elastic seal 3.

The openable/closable portion 29 constitutes the top end portion of the elastic seal 3 and has an approximately disk-like shape, and is disposed in the top portion of the small-diameter hole 12 of the body 7 and is located over the spike 2 and has a top end surface (approximately) flush with the top end surface of the body 7. The central portion of the bottom surface of the openable/closable portion 29 is made a concave surface 32 which is made hemispherical in an upwardly concave shape, and the concave surface 32 opposes the top end of the spike 2 across a gap. Incidentally, the concave surface 32 may also be placed in abutment with the top end of the spike 2. The concave surface 32 may also be placed in abutment with the peripheral surface of the straight portion 2A of the spike 2. The outside diameter of the openable/closable portion 29 is made (approximately) equal to or slightly smaller than the inside diameter of the small-diameter hole 11 of the body 7. A single (or two orthogonal) radial slit 33 is formed to extend longitudinally through the openable/closable portion 29 except the peripheral portion thereof, and the slit 33 can be opened by radially outward elastic deformation of the openable/closable portion 29.

The shrinkable portion 30 constitutes the greater part of the elastic seal 3 and has a bellows-like form, and is extended downwardly from the bottom surface of the openable/closable portion 29 and contains the spike 2. It is to be noted that when the elastic seal 3 is pressed downwardly by the tip of the male luer, the elastic seal 3 shrinks downwardly, and the greater part (or the whole) of this shrinkage is performed by the shrinkable portion 30.

The flange portion 31 constitutes the bottom end portion of the elastic seal 3 and has a ring-like shape, and is formed to project radially outwardly from the bottom end portion of the shrinkable portion 30. The flange portion 31 is fitted in the engagement hole 17 of the body 7, and is clamped and fixed between the abutment surface 16 of the body 7 and the mating portion 19 of the connector 8.

In the above-described embodiment, when fluid infusion, blood collection or the like is to be performed by means of the mixing plug, after the top end surface of the mixing plug has been sterilized, for example, a tip 38 of a syringe 37 which is shown as one example of a male luer is inserted into the small-diameter hole 12 of the body 7 of the housing 1 from the top end opening, as shown in FIGS. 4 and 5.

In this case, as shown by imaginary lines in FIG. 5, a syringe with a lock member 40 having a female screw portion formed around its inside surface is used as the syringe 37, and the syringe 37 can be positively maintained in the above-mentioned inserted state by screwing the female screw portion of the lock member 40 onto the male screw portion 11 of the body 7.

The elastic seal 3 is pressed by the above-mentioned insertion of the tip 38 of the syringe 37, and the shrinkable portion 30 and the like of the elastic seal 3 shrink against their resilient forces. During this time, since the spike 2 except at least the top end portion is made the tapered portion 2B which is formed in an (approximately) tapered shape so that the outside diameter becomes progressively smaller toward the top end and the outside diameter increases not stepwise but continuously in the downward direction, the shrinkable portion 30 and the like of the elastic seal 3 smoothly shrink during the shrinkage of the elastic seal 3 without being caught by a peripheral surface of the spike 2. In addition, since the elastic seal 3 except the openable/closable portion 29 and the flange portion 31 is made the bellows-shaped shrinkable portion 30, the elastic seal 3 smoothly shrinks for this reason as well.

By the above-mentioned shrinkage and the abutment between the slit 33 of the openable/closable portion 29 of the elastic seal 3 and the top end of the spike 2, as shown in FIG. 5, the openable/closable portion 29 is elastically deformed radially outwardly to open the slit 33 of the openable/closable portion 29, whereby the openable/closable portion 29 is fitted onto the top end portion of the tapered portion 2B of the spike 2 to expose the straight portion 2A of the spike 2 and the top end portion of the fluid transferring passages 28. Accordingly, since the inside of the syringe 37 communicates with the tube 26 via the fluid transferring passages 28 of the spike and the communication hole 22 of the connector 8, fluid infusion, blood collection or the like can be performed similarly to the case of the related art.

When fluid infusion, blood collection or the like are completed, the tip 38 of the syringe 37 is extracted from the body 7 of the housing 1. Accordingly, the shrinkable portion 30 and the like are expanded and restored to the original size by the resilient forces of the shrinkable portion 30 and the like of the elastic seal 3. During this time, since the spike 2 except at least the top end portion is made the tapered portion 2B which is formed in an (approximately) tapered shape so that the outside diameter becomes progressively smaller toward the top end, the shrinkable portion 30 and the like of the elastic seal 3 smoothly expand without being caught by a peripheral surface of the spike 2 in a manner similar to the above-mentioned one. In addition, since the elastic seal 3 except the openable/closable portion 29 and the flange portion 31 is made the bellows-shaped shrinkable portion 30, the elastic seal 3 smoothly expands for this reason as well. Furthermore, at the same time as this expansion, the openable/closable portion 29 also rises, and is restored to the original position. Accordingly, the slit 33 of the openable/closable portion 29 is closed, and the spike 2 is sealed by the elastic seal 3.

According to the above-mentioned embodiment, the fluid transferring passages 28 which are opened radially outwardly are formed on the spike 2, and even if, as in the case of the related art, the outside diameter of the spike 2 is made small in such a way that the fluid transferring passages 28 are not completely covered with the peripheral wall portion of the spike 2, there is no need for making the peripheral wall portion of the spike 2 extremely thin, whereby even the spike 2 having a small outside diameter can be easily formed from a resin or the like.

Accordingly, even in the case where the male luer is the syringe 37 made of glass and, the tip 38 is made of glass and is small in its inside diameter in the above-mentioned manner, the spike 2 can be easily inserted into the tip 38, whereby the syringe 37 and the mixing plug can be easily connected to each other.

Figure 6:
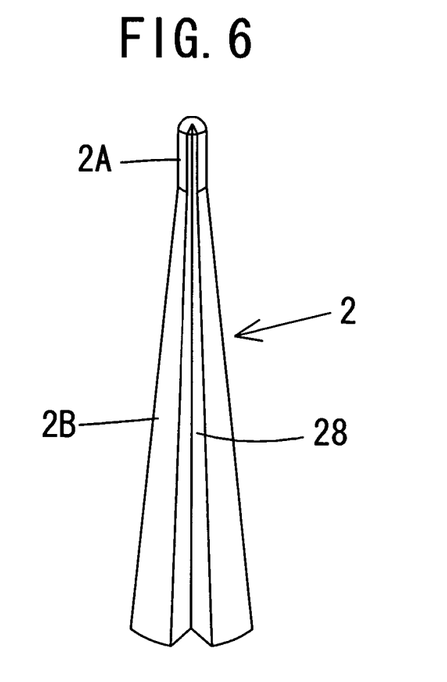
FIG. 6 is a perspective view showing a second embodiment of the invention.

FIG. 6 shows a second embodiment of the invention, and the fluid transferring passage 28 which is made a groove having a V-like cross-sectional shape is formed to extend in the peripheral surface of the solid spike 2 along the entire longitudinal length thereof. The fluid transferring passage 28 may be formed to extend along the entire longitudinal length of the spike 2 except the straight portion 2A. In addition, in this embodiment as well as third to fifth embodiments to be described later, as in the first embodiment as described above, the outside diameter of the tapered portion 2B is made progressively smaller toward the top end in a manner similar to the above-mentioned one, but the outside diameter may be made smaller not continuously but stepwise. In addition, the whole of the spike 2 may be made as described above.

In the above-mentioned embodiment, since the spike 2 is made solid and a groove having a V-like cross-sectional shape is simply formed in the peripheral surface of the spike 2 to constitute the fluid transferring passage 28, the strength of the spike 2 can be made large, and there is no risk that the spike 2 is deformed during the expansion, shrink and the like of the elastic seal 3.

Figure 7:
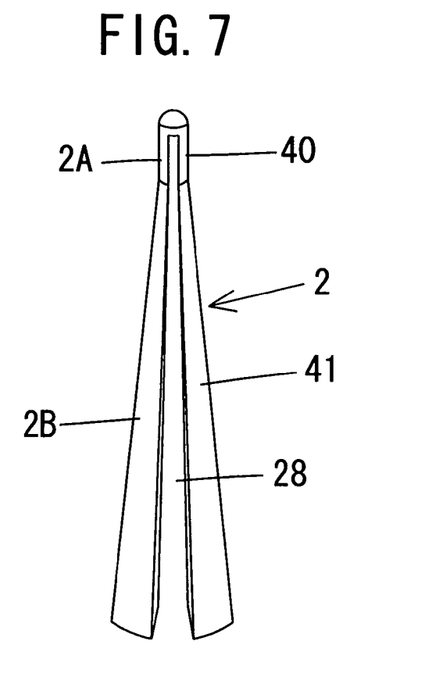
FIG. 7 is a perspective view showing a third embodiment of the invention.

FIG. 7 shows a third embodiment of the invention, and the spike 2 has a joining portion 40 and a plurality of (in the shown example, two) branch portions 41. The joining portion 40 constitutes the top end portion of the spike 2, and the remaining portion of the spike 2 is made of the branch portions 41. The branch portions 41 are formed integrally with the joining portion 40 and branch off in downward directions. The fluid transferring passage 28 is defined between the branch portions 41.

Figure 8:
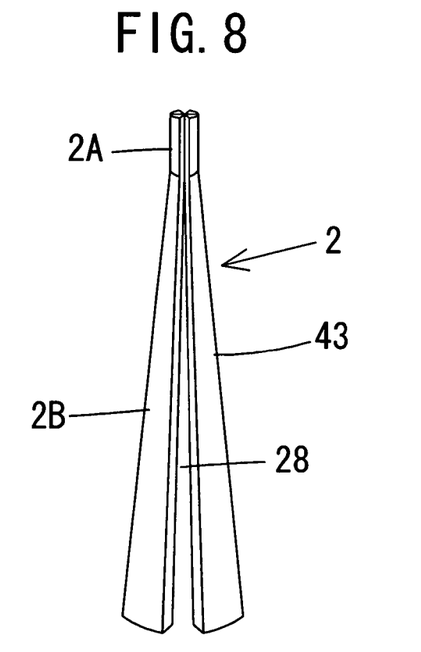
FIG. 8 is a perspective view showing a fourth embodiment of the invention.

FIG. 8 shows a fourth embodiment of the invention, and the spike 2 is made of a plurality of divided bodies 43 which extend along the entire longitudinal length of the spike 2. In this embodiment, the divided bodies 43 are formed into one pair in axial symmetry, and the fluid transferring passage 28 is defined between the divided bodies 43.

In the above-mentioned embodiment, since the construction of the spike 2 is simple, manufacturing can be easily performed.

Figure 9:
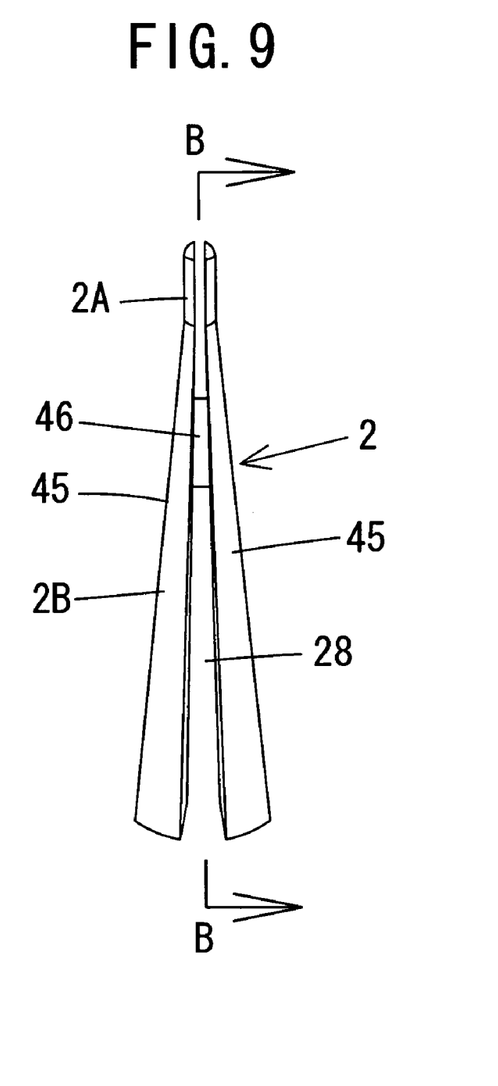
FIG. 9 is a perspective view.
Figure 10:
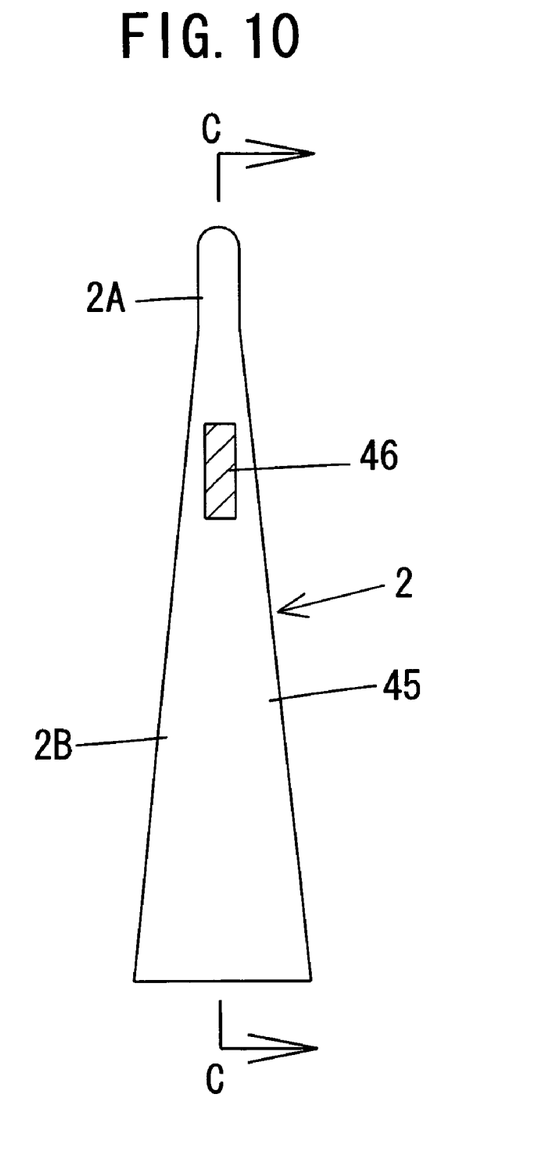
FIG. 10 is a cross-sectional view taken along line B-B of FIG. 9.
Figure 11:
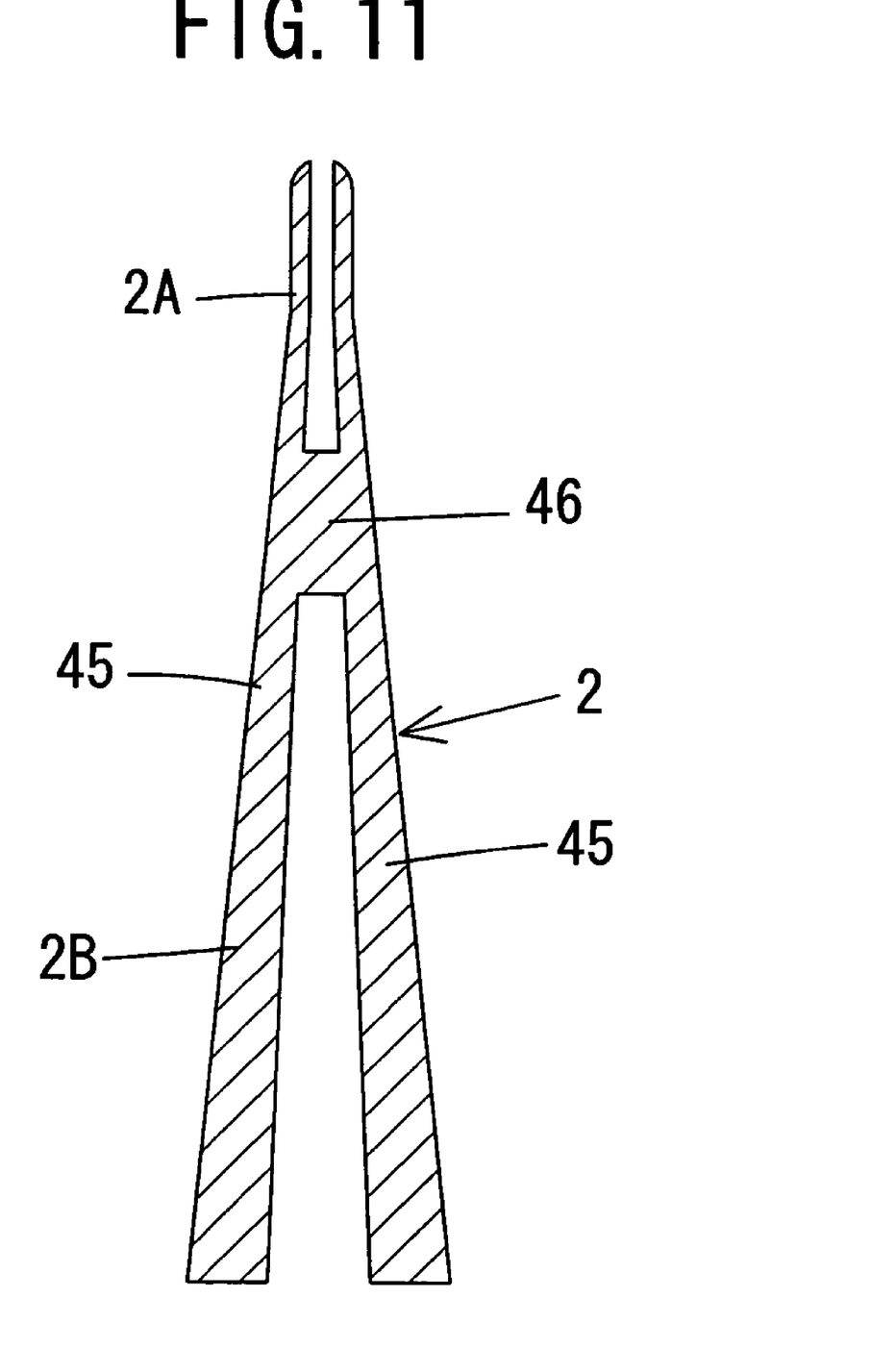
FIG. 11 is a cross-sectional view taken along line C-C of FIG. 10.

FIGS. 9 to 11 show a fifth embodiment of the invention, and the spike 2 has a plurality of (in the shown example, two) main portions 45 and a bridge portion 46. The main portions 45 are formed to extend along the entire longitudinal length of the spike, while the bridge portion 46 is formed integrally with the main portions 45 and is disposed between the main portions 45 to join these main portions 45 together. The fluid transferring passage 28 is defined between he main portions 45.

In the above-mentioned embodiment, as the bridge portion 46 is made larger, the strength of the spike 2 can be made higher and a dead space can be made smaller, whereas as the bridge portion 46 is made smaller, the spike 2 can be made smaller in diameter. Namely, it is possible to easily modify the performance of the spike 2, i.e., the mixing plug, by modifying the length and the thickness of the bridge portion 46 within a range which does not allow the bridge portion 46 to project outwardly from the spike 2.

Figure 12:
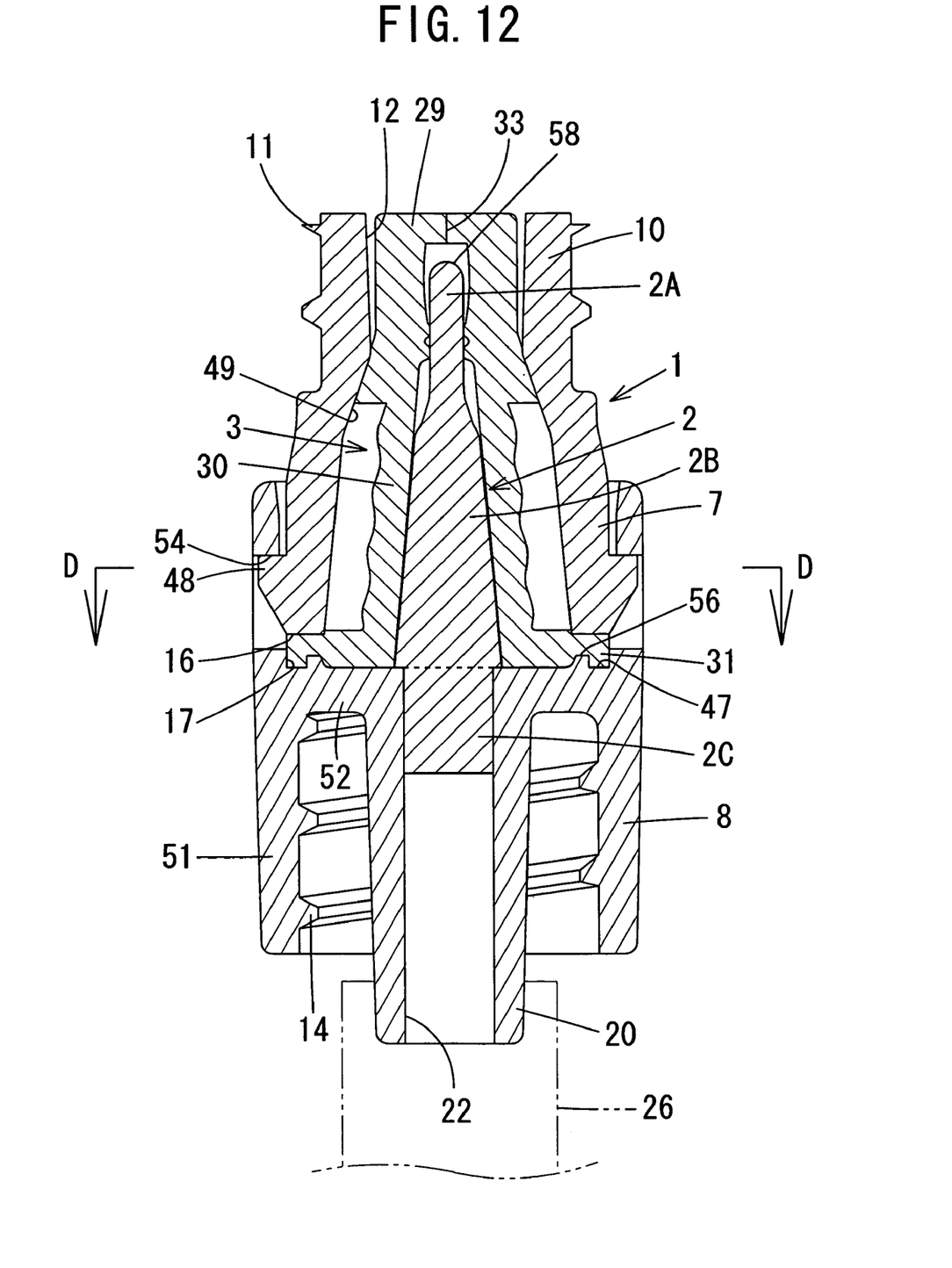
FIG. 12 is a cross-sectional view.
Figure 14:
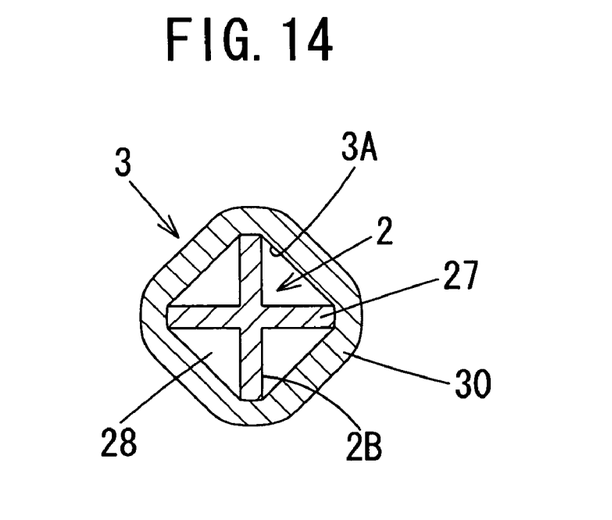
FIG. 14 is a cross-sectional view taken along line D-D of FIG. 12.
Figure 15:
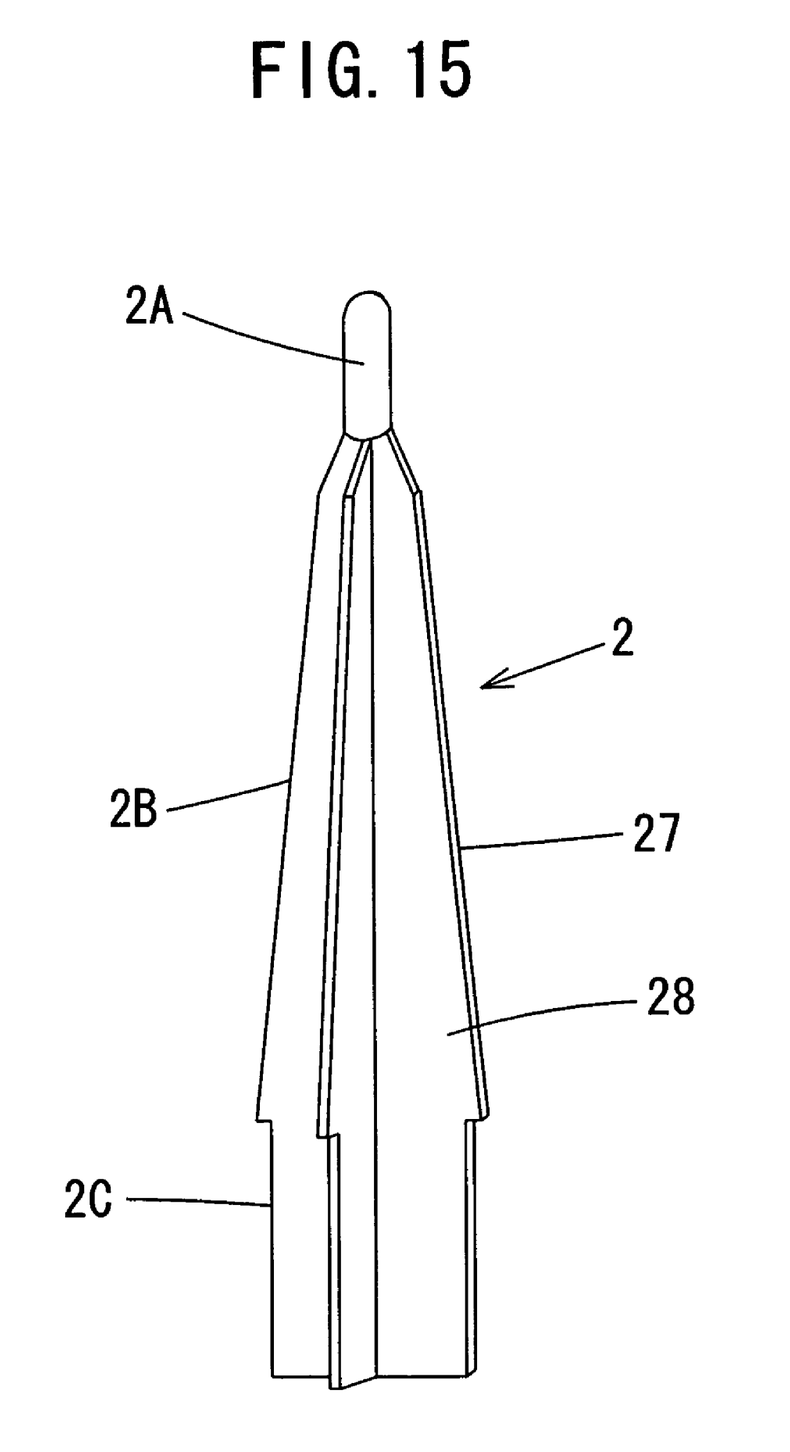
FIG. 15 is a perspective view of the spike of FIG. 12.
Figure 16:
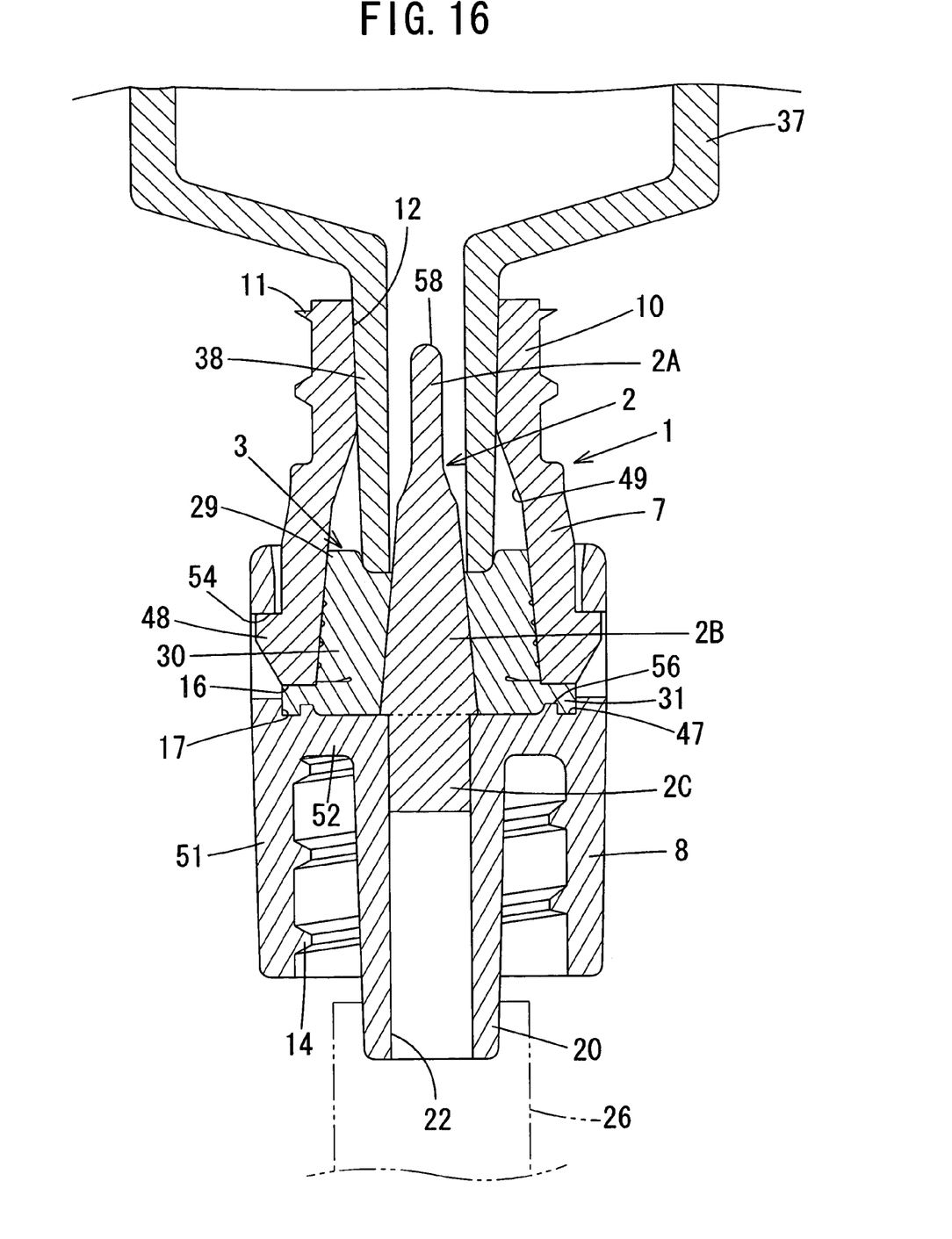
FIG. 16 is a view of the operating state of FIG. 12.

FIGS. 12 to 17 show a sixth embodiment of the invention, and as shown in FIGS. 12 and 16, the body 7 generally constitutes the top-portion side of the housing 1, and the bottom surface of the body 7 is made the abutment surface 16. A plurality of mating projections 48 which project radially outwardly are circumferentially spaced from one another at equal intervals around the peripheral portion of the bottom portion of the body 7. The inside surface of the body 7 except the small-diameter hole 12 in the top portion is made a tapered hole 49 which is tapered upwardly.

The connector 8 generally constitutes the bottom-portion side of the housing 1. The connector 8 is constructed by integrally forming an external tube portion 51 having a tubular shape disposed to extend in the longitudinal direction, the downstream-side connecting portion 20, and a ring portion 52. The downstream-side connecting portion 20 has a tubular shape opened in the longitudinal direction and is disposed to extend through the inside of the external tube portion 51 concentrically in the longitudinal direction, and the bottom-end portion of the downstream-side connecting portion 20 projects downwardly from the external tube portion 51. A longitudinally middle portion of the external tube portion 51 and the top end portion of the downstream-side connecting portion 20 are connected together by the ring portion 52 having a ring-like shape.

A plurality of mating holes 54 which are formed to extend radially through the external tube portion 51 are circumferentially spaced from one another at equal intervals around a peripheral portion of the external tube portion 51 above the ring portion 52, and the mating projections 48 of the body 7 are disengageably engaged with the mating holes 54 by elastic deformation, whereby the body 7 and the connector 8 are integrated. A portion of the inside surface of the external tube portion 51 which is adjacent to the ring portion 52 is made the engagement hole 17 in which the flange portion 31 of the spike 2 is fitted. A portion of the inside surface of the external tube portion 51 below the ring portion 52 is made the female screw portion 14 in which a female screw is formed.

The inside of the downstream-side connecting portion 20 is made the communication hole 22. In addition, the top surface of the downstream-side connecting portion 20 and the ring portion 52 is made an abutment surface 47, and this abutment surface 47 and the abutment surface 16 of the body 7 are brought into abutment with the flange portion 31 of the spike 2 to clamp this flange portion 31. Furthermore, a ring projection 56 which projects upwardly is integrally formed on the abutment surface 47, and this ring projection 56 bites the flange portion 31 of the spike 2 so that the flange portion 31 is more firmly fixed to the housing 1.

Figure 13:
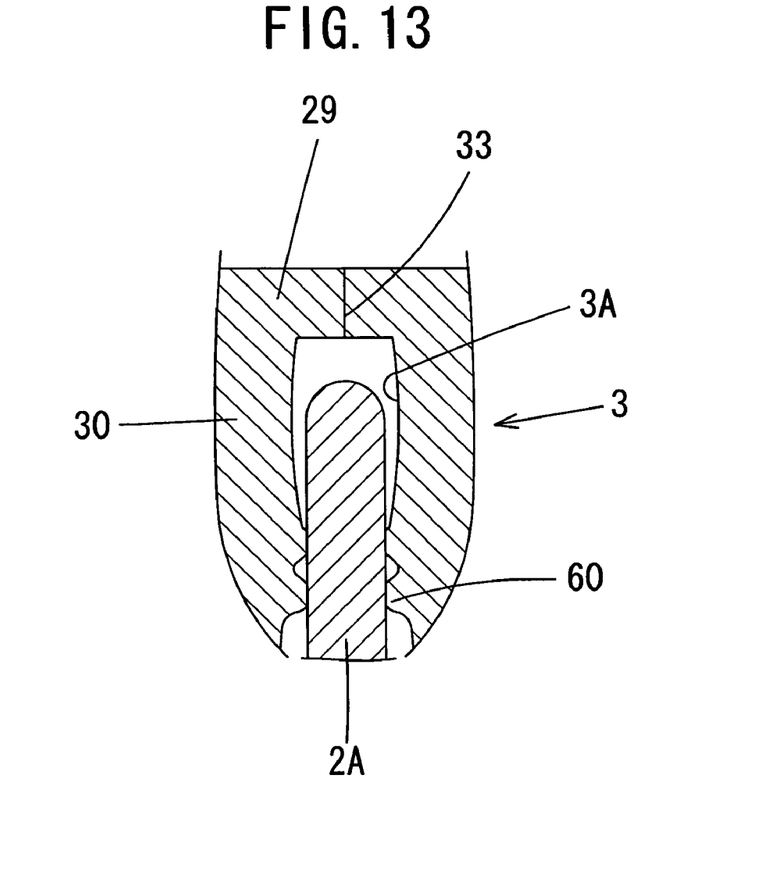
FIG. 13 is a partly enlarged view of FIG. 12.

The spike 2 has the straight portion 2A, the tapered portion 2B and an inserting portion 2C which are integrally formed to be arranged in named order in the downward direction, as shown in FIGS. 13 to 15 as well.

The straight portion 2A constitutes the top end portion of the spike 2 and has an approximately cylindrical solid structure having an approximately constant outside diameter, and the top end surface of the straight portion 2A is made an hemispherical surface 58 which is upwardly convex. Accordingly, since the top end surface of the straight portion 2A is made the hemispherical surface 58 which is upwardly convex, when the spike 2 comes into abutment with the openable/closable portion 29 of the elastic seal 3 to open the openable/closable portion 29, the openable/closable portion 29 is smoothly opened. Since the straight portion 2A which is the top end portion of the spike is made approximately cylindrical, the opening of the openable/closable portion 29 smoothly moves downwardly along the straight portion 2A of the spike 2 so that the openable/closable portion 29 can be smoothly opened and closed.

The tapered portion 2B constitutes the spike 2 except the top and bottom end portions and is formed in an (approximately) tapered shape so that its outside diameter becomes progressively smaller toward the top end.

The inserting portion 2C constitutes the bottom end portion of the spike 2, and is made smaller in diameter than the outside diameter of the bottom end of the tapered portion 2B and is made constant in outside diameter. The inserting portion 2C is inserted into the communication hole 22 of the connector 8 and is fixed to the inside surface of the communication hole 22 by an adhesive or by being fitted thereinto. Since the inserting portion 2C of the spike 2 is inserted into and fixed to the communication hole 22 of the connector 8, the spike 2 can be easily and firmly fixed to the housing 1.

The tapered portion 2B and the inserting portion 2C are made of at least three (in this embodiment, four) fins 27 which project radially outwardly from its axial portion. The fins 27 are circumferentially spaced from one another at equal intervals and the longitudinal fluid transferring passages 28 are defined between adjacent ones of the fins 27. Each of the fluid transferring passages 28 is opened radially outwardly and is also opened at both top and bottom ends. The bottom end opening of each of the fluid transferring passages 28 communicates with the communication hole 22 of the connector 8.

The elastic seal 3 is a modification of the elastic seal of the first embodiment, and has the openable/closable portion 29, the shrinkable portion 30 and the flange portion 31 which are integrally formed to be arranged in named order in the downward direction.

The shrinkable portion 30 does not have a bellows-like form, unlike the shrinkable portion 30 of the first embodiment. The inside surface of the shrinkable portion 30 is preferably made a smooth surface so that the shrinkable portion 30 can be smoothly fitted onto the spike 2. The top portion of the shrinkable portion 30 is made approximately constant in both inside and outside diameters, and an inside surface 3A of this top portion has one or a plurality of ring-shaped projections 60 formed to be arranged in the longitudinal direction as shown in FIG. 13. The ring-shaped projections 60 are formed to project radially inwardly from the inside surface of the shrinkable portion 30 and to extend around (approximately) the entire circumference of the inside surface 3A of the shrinkable portion 30. At least one of these ring-shaped projections 60 is placed in abutment with the straight portion 2A of the spike 2, whereby the pressure resistance (strength) of the openable/closable portion 29 of the elastic seal 3 can be enhanced to prevent accidental opening of the openable/closable portion 29.

The shrinkable portion 30 except the top portion is formed in an (approximately) tapered shape so that its inside and outside diameters become progressively smaller toward the top end. The outside contours of the longitudinal cross-section of the bottom-portion side of the shrinkable portion 30 is made wavy so that the shrinkable portion 30 easily expands and shrinks.

Figure 17:
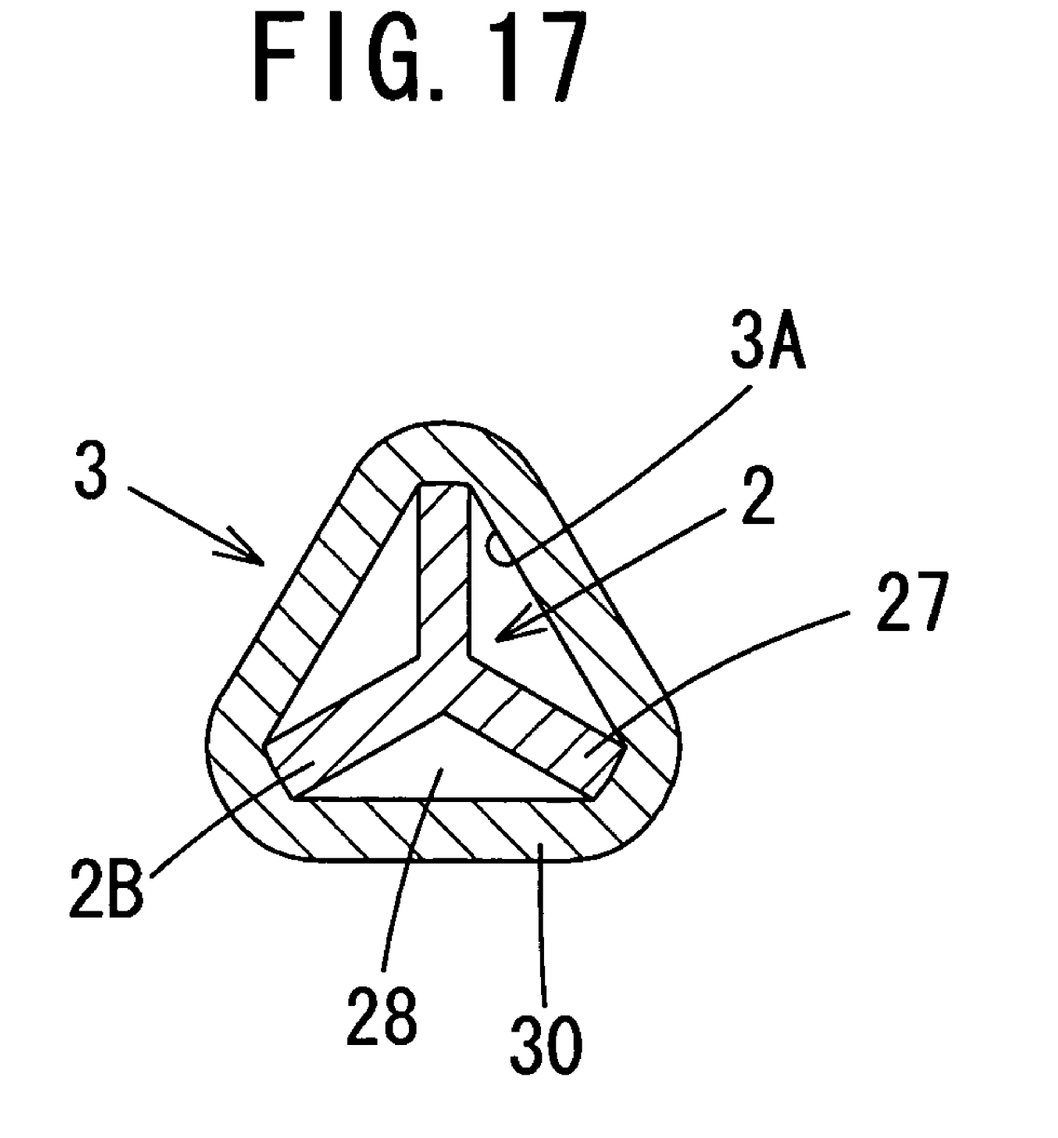
FIG. 17 is a view of a modification of the invention shown in FIG. 14.

Incidentally, it is preferable that an edge which is located on the outermost side of each of the fins 27 of the tapered portion 2B of the spike 2 be placed in abutment with the inside surface 3A of the elastic seal 3, because it is possible to decrease the volume (or medical-valve volume or dead space) of the mixing plug in the inside of the elastic seal 3 and it is possible to decrease the amount of backflow of a medicament solution which occurs when the tip 38 of the syringe 37 which is shown as one example of a male luer is separated from the mixing plug. For this reason, in this embodiment, for example, the inside diameter of the elastic seal 3 is made smaller than the minimum outside diameter of the fins 27, and the elastic seal 3 is fitted onto the spike 2 while it is being elastically deformed, whereby the outside surface of the fins 27 of the tapered portion 2B of the spike 2 is brought into abutment with the inside surface 3A of the elastic seal 3. At this time, a portion of the elastic seal 3, which is brought in abutment with the fins 27, has a cross section of an approximately polygonal shape. As shown in FIG. 14 by way of example, if the number of the fins 27 of the spike 2 is four, the portion of the elastic seal 3, which is brought in abutment with the fins 27, has a cross section of an approximately quadrilateral shape, while as shown in FIG. 17 by way of example, if the number of the fins 27 of the spike 2 is three, the portion of the elastic seal 3, which is brought in abutment with the fins 27, has a cross section of an approximately triangular shape. The outside diameter of each portion of the spike 2 is defined as follows. Namely, the smallest circuit that passes part of the outermost edge of each portion of each of the fins 27 is assumed, and the diameter of the circle is made the outside diameter of each portion of the spike 2. Incidentally, the portion of the elastic seal 3, which comes into abutment with the fins 27, may be previously made an approximately polygonal shape corresponding to the number of the fins 27.

It is to be noted that the housing of the first embodiment and the spike and the elastic seal of the sixth embodiment may also be combined, or the spike and the elastic seal of the first embodiment and the housing of the sixth embodiment may also be combined.

In each of the embodiments, when the syringe is extracted from the housing, the elastic seal expands by the resilient force of the elastic seal, and a metal spring, a resin spring or the like may also be used in combination for the purpose of assisting with this expansion. In addition, although in each of the embodiments the invention is applied to the mixing plug, the invention can be applied to various other kinds of medical valves.

What is claimed is:

1. A medical valve, to which a male luer is to be separably connected, comprising:
    (a) a housing having a hollow body opened at the top end, wherein the tip of the male luer is to be removably inserted in the housing;
    (b) a longitudinal solid spike disposed to extend longitudinally in the housing, the spike except at least the top end portion being formed in a shape approximately tapered upwardly, wherein a groove-shaped fluid transferring passage, which extends the entire longitudinal length of the spike is formed on the outer peripheral surface of the spike, the bottom portion of the fluid transferring passage being connected to a fluid circuit; and
    (c) an elastic seal having an elastically deformable tubular shape fitted on the spike to seal the spike, the elastic seal comprising a top end portion having an openable/closable portion to be openably closed over the spike, wherein the elastic seal is elastically deformed to be downwardly compressed by downward pressure due to the tip of the male luer, thereby the openable/closable portion is brought into abutment with the spike, and is elastically deformed to be opened radially outwardly to be fitted onto the spike, so that the inside of the male luer communicates with the fluid transferring passage of the spike.

2. A medical valve according to claim 1, wherein the spike comprises at least three longitudinally extending fins projecting radially outwardly from the axial portion,
    and wherein fluid transferring passages are defined between adjacent ones of the fins and an inner surface of the elastic seal.

3. A medical valve according to claim 2, wherein the fins are circumferentially spaced from one another at equal intervals,
    the edge of each of the fins being placed in abutment with the inner surface of the elastic seal.

4. A medical valve according to claim 3, wherein a portion of the elastic seal, which is brought in abutment with the fins, has a cross section of an approximately polygonal shape.

5. A medical valve according to claim 1, wherein the bottom portion of the spike is inserted in and fixed to the housing.

6. A medical valve according to claim 1, wherein the central portion of the bottom surface of the openable/closable portion is made approximately flat and is opposed to the top end of the spike across a gap.

7. A medical valve according to claim 1, wherein a ring-shaped projection, which projects radially inwardly and is placed in abutment with the top end portion of the spike, is formed to extend around approximately the entire circumference of an inner surface of the top portion of the elastic seal.

8. A medical valve according to claim 1, wherein the elastic seal except the openable/closable portion and the bottom end portion has a bellows-shaped shrinkable portion.

9. A medical valve according to claim 1, wherein the top end surface of the housing and the top end surface of the elastic seal are made substantially flush with each other.

* * * * *